United States Patent [19]
Stima

[11] 3,978,860
[45] Sept. 7, 1976

[54] TABS FOR DISPOSABLE DIAPERS

[75] Inventor: Joseph Frank Stima, Edison, N.J.

[73] Assignee: Colgate-Palmolive Company, New York, N.Y.

[22] Filed: July 31, 1975

[21] Appl. No.: 600,877

[52] U.S. Cl. ................................ 128/284; 128/287
[51] Int. Cl.² ...................... A41B 13/02; A61F 13/16
[58] Field of Search ........... 128/155, 156, 284, 287, 128/290 R

[56] References Cited
UNITED STATES PATENTS

| | | | |
|---|---|---|---|
| 3,422,570 | 1/1969 | Vorst et al. | 128/155 X |
| 3,630,201 | 2/1971 | Endres | 128/287 |
| 3,867,940 | 2/1975 | Mesek | 128/284 X |

*Primary Examiner*—Aldrich F. Medbery
*Attorney, Agent, or Firm*—Norman Blumenkopf; Herbert S. Sylvester; Murray M. Grill

[57] ABSTRACT

A disposable diaper comprising a body of absorbent material defined by peripheral edges and having an inside surface for direction toward the body of an infant. There is provided at least one adhesive tape tab affixed to the diaper along a peripheral edge, said tab comprising a strip of tape with adhesive material on one side and having a pad of gauze cushioning material along its peripheral edge.

7 Claims, 3 Drawing Figures

TABS FOR DISPOSABLE DIAPERS

BACKGROUND OF THE INVENTION

1. Field of the Invention

This invention relates to disposable diapers having adhesive tape tab fasteners.

2. Description of the Prior Art

Conventional disposable diapers comprise a rectangular back sheet of waterproof material, a rectangular absorbent pad and a rectangular top sheet of hydrophobic material. The back sheet is generally wider than the pad and the top or face sheet and the longitudinal edges of the back sheet extend past the longitudinal edges of the pad and the face sheet. The back sheet is folded around the edges of the pad and onto the face sheet forming side flaps. The longitudinal edges of the back sheet are then adhered to the face sheet.

In order to successfully meet consumer expectations a disposable diaper must, as an assembly, have sufficient strength to prevent tearing when applied and when worn by an infant and must also have sufficient limpness or ability to be molded or adjusted by hand to fit closely around the thighs and trunk of an infant. This limpness, or ability to be molded or adjusted by hand, is required in order to create a seal to contain discharged urine in order to give the absorbent pad sufficient time to absorb the urine. Failure to provide these features results in a products which causes soiled clothing, infant discomfort and a general adverse reaction on the part of the consumer.

Present disposable diapers attempt to meet the above goal of having sufficient strength to avoid tearing by providing the above mentioned folded edge of back sheet on each of the longitudinal edges of the diaper. The back sheet on one form of conventional disposable diaper has side flaps which are folded, one each, around the longitudinal edges of the absorbent pad and are fastened to the face sheet by adhesive means. In this form of conventional disposable diaper the combined width of the side flaps are equal to approximately two thirds of the overall width of the diaper in the folded configuration. The side flaps are placed in a complex state of combined bending and tensile stress when the conventional disposable diaper is applied. Adhesive tabs are used for applying the disposable diaper. Pressure sensitive adhesive tape tabs have been used in the past in place of pins or other fastening means for securing diapers in place on infants. Such an adhesive tape tab is disclosed in the U.S. Pat. No. 3,776,234 of Raymond M. Hoey issued Dec. 4, 1973 and entitled "Disposable Diaper with Adhesive Tape Tab Fasteners". In the foregoing patent such an adhesive tape tab fastener includes an easily removable release sheet over portions of the adhesive tape.

When a child who is wearing a disposable diaper having adhesive tape tab fasteners evacuates or through movement of the body, causes the diaper to slip down on the body, the adhesive tape tabs of all of the prior art give "paper" cuts of chafe.

SUMMARY OF THE INVENTION

The concept of the present invention resides in attaching a soft material to the bottom edge, along all or most of the periphery of the adhesive tape tab whereby the soft material acts as a cushion and does not cut into the infant's skin. The cushion is attached on the tab by the same adhesive used to make the seal when securing the diaper on the infant. Accordingly, it is an object of this invention to provide a disposable diaper having adhesive tape tab fasteners which will not cut or chafe the infant on which the diaper is used.

Another object of this invention is to provide a disposable diaper having pressure sensitive adhesive tape tabs with a peripheral gauze pad secured to the adhesive for preventing paper cuts while also providing a convenient way to open the tabs.

A further object of the invention resides in the provision of a disposable diaper formed of a body of absorbent material defined by its peripheral edges and having an inner surface for placement next to the body of an infant wearing the diaper, and having one or more tape tabs for holding the diaper closed around the infant. Each adhesive tape tab is affixed to the diaper along an edge thereof and comprises a strip of tape with pressure sensitive adhesive material on one side thereof and having a peripheral gauze pad affixed to the adhesive along all or most of the peripheral edges. A removable release sheet may be provided as desired.

These, together with the various ancillary objects and features of the invention which will become apparent as the description proceeds are attained by these improved tabs for disposable diapers, a preferred embodiment being illustrated in the accompanying drawings, by way of example only, wherein:

DETAILED DESCRIPTION OF THE INVENTION

Figure 1:
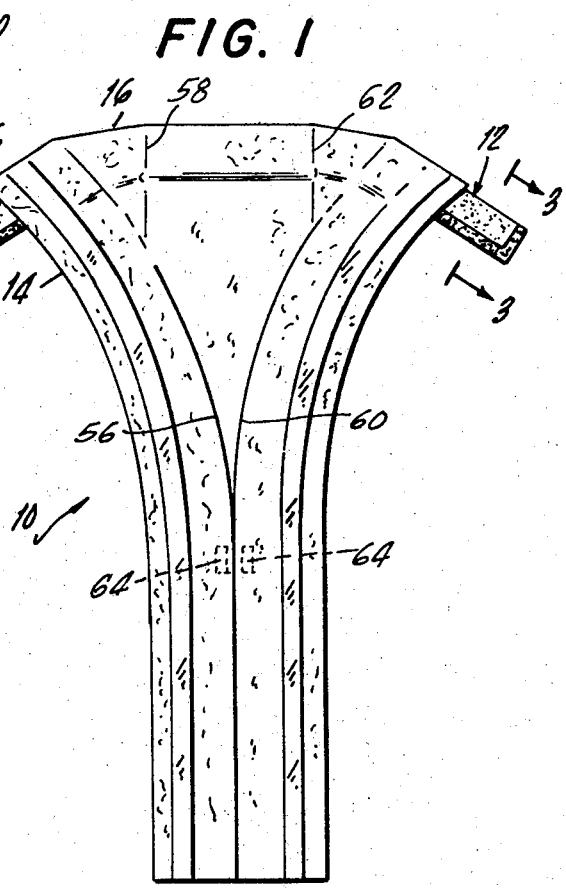
FIG. 1 is a plan view of a diaper constructed in accordance with the concepts of the present invention shown in a partially spread position prior to positioning on an infant.

With continuing reference to the accompanying drawing wherein like reference numerals designate similar parts throughout the various views, reference numeral 10 is used to generally designate a disposable diaper formed of a body of absorbent material having adhesive tape tab fasteners of the concept of the present invention. The disposable diaper 10 has tape tabs 12 attached to the diaper at its side edges 14 near the end edges 16. The inside surface 18 is of a soft absorbent material for placement next to the body of an infant wearing the diaper to absorb waste material.

The tab 12 comprises a strip of adhesive tape 20 having a layer 22 of pressure sensitive adhesive material on one side thereof Each strip 20 is affixed to a marginal portion of the diaper. In use, the adhesive tape tab 12 will normally hold the sides 14 of the diaper together. However, when the infant wets, defecates or moves his body in various manners, the side edges 14 may part and the adhesive tape tab can touch the skin of the infant and can cause chafing of "paper" cuts. These are avoided by the concept of the present invention in providing a cushioning pad 24 of a gauze or the like. The bottom edge of the gauze 24 can be feathered at 26 to make it softer. In addition, the tab 12 can be made from a relatively soft or less rigid material than the adhesive tab heretofore employed. A release sheet 30 is easily removably affixed to the exposed portions of the adhesive and overlies the feathered surface 26.

Figure 2:
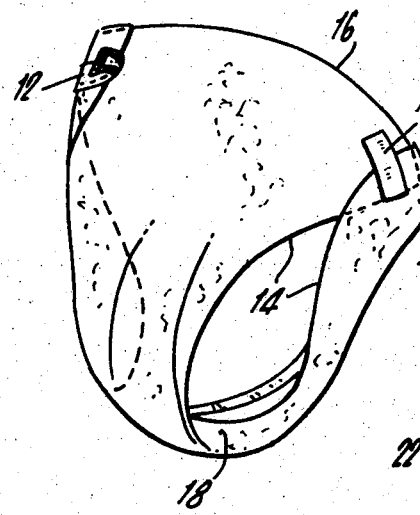
FIG. 2 is a perspective view of the diaper in the form it may take when secured on an infant.
Figure 3:
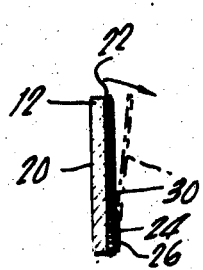
FIG. 3 is an enlarged sectional detail view taken along the plane of line 3 in FIG. 1.

The disposable diaper 16 according to the present invention is provided in a pre-folded configuration shown in FIG. 1. This pre-folded configuration is accomplished through the use of longitudinal and parallel folds 56, 58, 60 and 62. The disposable diaper is folded inwardly along the folds 58 and 60 and is folded outwardly along the folds 56 and 62. The folds 56, 58, 60 and 62 are disposed so that when in the pre-folded condition, the folds 56 and 62 are spaced. When the disposable diaper 10 is about to be applied to an infant one end is fanned out by gently opening the folds 56, 58, 60 and 62 along approximately one half the length of the disposable diaper 10. Adhesive spots 64 and 66 may be provided approximately centered along the length of the disposable diaper 10 and are disposed to adhere the portion of the disposable diaper between the folds 56 and 58 and the portion of the disposable diaper between the folds 60 and 62 each onto the portion of the disposable diaper between the folds 56 and 60. Adhesive spots 64 and 66 assist in unfolding the pre-folded disposable diaper to the configuration shown in FIG. 1. After the disposable diaper 10 is unfolded into the configuration shown in FIG. 1 the infant is placed on the disposable diaper 10 with his buttock slightly closer to the fanned out end and the unfanned out end is brought up between his legs and also fanned out. The opposite ends of the disposable diaper 10 are then brought together and the tape fasteners 12 are used to asecure the ends of the disposable diaper 10 to each other as shown in FIG. 2.

A latitude of modification, substitution and change is intended in the foregoing disclosure and in some instances, some features of the invention will be employed without a corresponding use of other features.

I claim:

1. A disposable diaper comprising a body of absorbent material defined by peripheral edges and having an inside surface for direction toward the body of an infant, and at least one adhesive tape tab affixed to the diaper along a peripheral edge, said tab comprising a strip of tape with pressure sensitive adhesive material on one side thereof and having a pad of cushioning material along its peripheral edge.

2. A disposable diaper according to claim 1, wherein said pad is of gauze.

3. A disposable diaper according to claim 1, including a release sheet secured to said adhesive material and overlying said pad.

4. A disposable diaper according to claim 1, wherein said pad has a feathered outer surface.

5. A disposable diaper according to claim 1, wherein said pad is of gauze, and a release sheet secured to said adhesive and overlying said pad.

6. A disposable diaper according to claim 1, wherein said pad is of gauze, the outer surface of said gauze being feathered.

7. A disposable diaper according to claim 6, including a release sheet secured to said adhesive material and overlying said feathered outer surface of said pad.

* * * * *